United States Patent [19]

Schwarze et al.

[11] Patent Number: 4,621,121

[45] Date of Patent: Nov. 4, 1986

[54] VULCANIZABLE MIXTURE CONTAINING BIS-(2-ETHYLAMINO-S-TRIAZIN-6-YL)-TETRASULFIDE

[75] Inventors: Werner Schwarze, Frankfurt am Main; Siegfried Wolff, Bornheim-Merten; Hans Remmel, Freigericht; Horst Lambertz, Hürth, all of Fed. Rep. of Germany

[73] Assignee: Degussa Aktiengesellschaft, Frankfurt, Fed. Rep. of Germany

[21] Appl. No.: 693,343

[22] Filed: Jan. 22, 1985

[30] Foreign Application Priority Data

Oct. 19, 1984 [DE] Fed. Rep. of Germany ....... 3438290

[51] Int. Cl.$^4$ .............................................. C08F 8/34
[52] U.S. Cl. ................................ 525/329.3; 524/262; 524/263; 524/265; 525/331.1; 525/331.8; 525/332.6; 525/332.7; 525/348

[58] Field of Search ............... 525/331.8, 332.9, 333.1, 525/342, 329.3, 348, 332.6, 353, 332.7, 331.1

[56] References Cited

U.S. PATENT DOCUMENTS 3,635,903  1/1972  Kearnan .............................. 525/348
3,801,537  4/1974  Westlinning ........................ 525/348

FOREIGN PATENT DOCUMENTS 1669954  10/1973  Fed. Rep. of Germany .

*Primary Examiner*—Christopher Henderson
*Attorney, Agent, or Firm*—Cushman, Darby & Cushman

[57] ABSTRACT

The invention is directed to bis-(2-ethylamino-4-diethylamino-s-triazin-6-yl)-tetrasulfide and a process for its production from the corresponding mercaptotriazine. The compound of the invention is employed in vulcanizable mixtures as a cross-linker or as vulcanization accelerator.

12 Claims, No Drawings

VULCANIZABLE MIXTURE CONTAINING BIS-(2-ETHYLAMINO-S-TRIAZIN-6-YL)-TETRASULFIDE

BACKGROUND OF THE INVENTION

The invention is directed to bis-(2-ethylamino-4-diethylamino-s-triazin-6-yl)tetrasulfide (V 480), a process for its production, its use, and vulcanizable mixtures containing it. The corresponding disulfide is known from German Pat. No. 1,669,954 and the related Westlinning U.S. Pat. No. 3,801,537. The entire disclosure of Westlinning is hereby incorporated by reference and relied upon. The disulfide can be produced for example from the corresponding mercaptotriazine by oxidation with iodine or hydrogen peroxide. The compound thus obtained is employed as a vulcanization accelerator in rubber mixtures.

The problem to be solved by the invention is to find a compound which imparts better properties to vulcanizates and process for the production of the compound.

SUMMARY OF THE INVENTION

The subject matter of the invention is bis-(2-ethylamino-4-diethylamino-s-triazin-6-yl)tetrasulfide (V 480) and a process for its production which comprises reacting an aqueous, alkaline solution of 2-ethylamino-4-diethylamino-6-mercaptotriazine in a 2-phase system with a solution of $S_2Cl_2$ in an inert organic solvent at a temperature of $< +10°$ C., with the proviso that the solvent either does not dissolve the tetrasulfide or only slightly dissolves it.

Advantageously there is produced an alkaline aqueous solution of the mercaptotriazine which contains the alkali ions (e.g. sodium or potassium ions) and mercaptotrazine molecule in equimolar amounts.

However, preferably there is used an amount of alkali, especially sodium hydroxide which is about 5 to 10% higher.

This solution is mixed with an organic solvent, especially an aliphatic or cycloaliphatic hydrocarbon, especially benzene (gasoline), petroleum ether or cyclohexane, so that there is formed a 2-phase system and there is added a solution of $S_2Cl_2$, preferably in the solvent which also is premixed beforehand with the solvent for the mercaptotriazine. The temperature thereby should be below 10° C., preferably below 5° C.

$S_2Cl_2$ is brought to reaction in equimolar amounts under vigorous stirring. Under the stated conditions the $S_2Cl_2$ surprisingly acts exclusively in a condensing manner. The molar ratio of $S_2Cl_2$ to the mercaptotriazine is preferably from 1:1 to 1,01:1, especially from 1:1 to 1,1:1.

The product which precipitated was separated with the help of commonly known procedures and dried advantageously at 40°-45° C. under a vacuum.

Other subject matter of the invention include the use of V 480 in vulcanizable rubber mixtures and the corresponding V 480 containing mixtures themselves.

In the use of the compound V 480 of the invention as cross-linker or vulcanization accelerator it clearly shows its superiority to the standard compounds as well as to the disulfide V 143.

There is an extensive palatte of accelerators available to the rubber processing industry, especially for sulfur vulcanization, of which the most important classes for all purpose rubbers are: benzthiazolylsulfenamide, bis-benzthiazolyldisulfide, and 2-mercaptobenzothiazole as well as their corresponding triazine derivatives. Besides there is a series of special compounds such as thiuramdisulfides and peroxides which also act as cross-linkers without further additives such as sulfur, but which also are frequently used in combination with sulfur.

Today, the quantitatively most significant in terms of practical use, especially for the vulcanization of all purpose rubbers are the benzthiazolylsulfenamides.

A substantial disadvantage of the just mentiond vulcanization accelerators, especially the sulfenamides, is their greatly increasing tendency to reversion of the vulcanizate with increasing vulcanization temperature, especially when using besides reversion susceptible types of rubber such as NR and polyisoprene. With increasing temperature the speed of reversion increases so greatly that on the one hand there is a drastic reduction of the cross-linking density at optimum vulcanization and on the other hand, there is a sharp decline of the optimum cross-linking density with a frequently unavoidable over vulcanization. This is of similar concern but applies to a lesser extent to the remaining accelerator of the class of benzothiazoles.

These disadvantages of the benzothiazole accelerators limit their usability with increasing vulcanization temperature and places limits in reference to the efforts of the processing industry to increase productivity by the use of higher vulcanization temperatures.

A further non-neglibible disadvantage today, especially of the sulfenamides, is that there is formed free amine during the vulcanization process, which, insofar as they are nitrosizable, can lead to the formation of toxic nitrosamines, which in the future can be expected to limit their areas of use through legislation.

Surprisingly V 480 proves to be a compound both in regard to its use as a cross-linker and also as a vulcanization accelerator in sulfur vulcanization, which imparts to the vulcanizates produced therewith even at high vulcanization temperatures extraordinarily high reversion resistance. Therefore, they are predestined for use with high temperature vulcanization and therewith make possible increases in productivity.

The use of V 480 includes known rubber mixtures according to the state of the art such as natural rubber (NR), isoprene rubber (IR), styrene-butadiene rubber (SBR), isobutylene isoprene rubber (IIR), ethylene-propylene-terpolymer rubber (EPDM), nitrile rubber (NBR), halogen containing rubber (e.g. polychloroprene or chlorinated natural rubber) and especially natural rubber which is epoxidized up to 75% (ENR), as well as their mixtures. The presence of double bonds is essential. The use of V 480 has particular significance of the reversion susceptible isoprene and natural rubbers, as well as their blends with other rubbers, V 480 is employed in sulfur containing rubber mixtures in an amount of 0.3 to 15, preferably 0.3 to 5 parts by weight per 100 parts of rubber.

In sulfur-free rubber mixtures there is used in an amount of 0.3 to 10, preferably, 0.3 to 5 parts by weight of V 480 per 100 parts by weight of rubber.

The rubber mixtures also contain the customary reinforcing system, i.e. furnace blacks, channel blacks, flame blacks, thermal blacks, acetylene blacks, arc blacks, (K blacks etc. as well as synthetic fillers such as silicas, silicates, aluminum oxide hydrate, calcium carbonate, and natural fillers such as clays, siliceous chalks, chalks, talcs, etc, and their blends in an amount of 5 to 300 parts per 100 parts of rubber ZnO and stearic acid as vulcanization promoters in an amount of 2 to 5 parts, customarily used antiagers, ozone protectants and fatigue protectants such as, e.g. IPPD, TMQ, as well as waxes as light protectants and their blends, plastizers at pleasure such as e.g. aromatic, naphthenic, parrafinic, synthetic plasticizers, and their blends optionally retarders such as e.g. N-cyclohexylthiophthalimide, (N-trichloromethylthiophenylsulfonyl)-benzene and their blends, optionally silanes such as e.g. bis-(3-triethoxysilylpropyl)-tetrasulfide, gamma-chloropropyltriethoxysilane, gamma-mercaptopropyltrimethoxysilane,

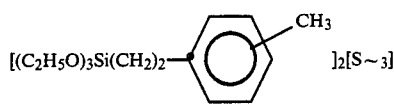

and their blends, in an amount of 0.1 to 20, preferably 1 to 10 parts per 100 parts of filler, optionally sulfur in an amount of 0.5 to 4 parts per 100 parts of rubber, optionally other customary accelerators customarily employed as secondary accelerators in the rubber industry, especially Vulkalent E, in an amount of 0.2 to 4 parts, preferably 0.6 to 1.8 parts based on 100 parts of rubber, optionally additional sulfur donors, optionally dyes and processing aids.

The vulcanizable composition can contain 0.3 to 15 parts of V 480 and also contain (N-trichloromethylthiophenylsulfonyl)-benzene in a 1:1 molar ratio to the V 480 and sulfur in an amount of 0.2 to 4 parts based on 100 parts of the rubber.

The area of use extends to rubber mixtures, as they are customarily used in making tires, to industrial articles, such as e.g. mixtures for conveyor belts, V-belts, molded articles, piles with or without insertions, rubber rolls, linings, spray profiles, freehand articles, films, shoe soles and uppers, cables, full gum tires, and their vulcanizates.

Unless otherwise indicated all parts and percentages are by weight.

The compositions can comprise, consist essentially of, or consist of the stated materials and the process can comprise, consist essentially of, or consist of the recited steps with such materials.

While V 480 can be used with advantage in high temperature vulcanization it also can be used with conventional lower temperature vulcanization.

DETAILED DESCRIPTION

EXAMPLE 1

454 grams of 2-diethylamino-4-ethylamino-6-mercaptotriazine were dissolved in aqueous sodium hydroxide which had been produced from 84 grams of NaOH and $\neq$1.5 liters of water.

The solution was placed in a liter three-neck flask, then there was added 1.5 liters of light benzine (B.P. 80°–110° C.) and the mixture cooled to 0° C. with vigorous stirring.

There was then run in within 20 minutes a solution of 137 grams of $S_2Cl_2$ in 100 ml of benzine whereby care was taken that the temperature did not exceed +50° C.

The tetrasulfide immediately precipitated out. At the end of the reaction the mixture was stirred for a further 5 minutes, subsequently sucked off and washed.

The snow white of fine powder was dried in a vacuum/12 Torr at 40°–45° C. Amount: 499.5 grams, corresponding to 97.1% of theory; M.P. 149°–150° C.

Analysis: Bis-(2-Ethylamino-4-diethylamino-s-triazine-6-yl)tetrasulfide, Mol-Wt. 516, $C_{18}H_{32}N_{10}S_4$

|  | C | H | N | S |
|---|---|---|---|---|
| Calculated | 41.9 | 6.2 | 27.1 | 24.8 |
| Found | 41.8 | 6.5 | 26.8 | 24.8 |

Testing Standards

The physical tests were carried out at room temperature according to the following standard specification (DIN stands for German Industrial Standard):

| | | |
|---|---|---|
| Tensile strength, elongation at break and on 6 mm thick rings modulus | DIN 53504 | MPa |
| Resistance to tear propagation | DIN 53507 | N/mm |
| Impact elasticity | DIN 53512 | % |
| Shore A hardness | DIN 53505 | — |
| Mooney Test, ML 4 | DIN 53524 | — |
| Goodrich Flexometer (Determination of heat build-up ΔT) | ASTM D 62362 | °C. |
| Firestone - Ball Rebound | AD 20245 | |

In the use examples there are employed the following names and abbreviations whose meanings are given below:

| | |
|---|---|
| RSS: | Ribbed Smoked Sheet (natural rubber) |
| Corax$^R$ N 220: | Carbon Black, Surface Area (BET) 120 m$^2$/g (Degussa) |
| Naftolen ZD: | Hydrocarbon Plasticizer |
| Ingralen 450: | Aromatic hydrocarbon plasticizer |
| Ingroplast NS: | Naphthenic hydrocarbon plasticizer |
| Vulkanox 4010 NA: | N—Isopropyl-N'—phenyl-p-phenylene-diamine |
| Vulkanox HS: | Poly-2,2,4-trimethyl-1,2-dihydroquinoline |
| Mesamoll: | Alkylsulfonic acid ester of phenyl and cresol |
| Protektor G35: | Wax protector against ozone |
| Vukacit MOZ: | N—Morpholine-2-benzothiazolsulphenamide |
| Vulcacit Mercapto: | 2-Mercaptobenzothiazole |
| Vulcacit Thiuram: | Tetramethyl-thiurammonosulfide |
| Vulcazit CZ: | N—Cyclohexyl-2-benzothiazolesulphenamide |
| Vulcalent E: | (N—trichloromethylthiophenylsulfonyl)-benzene |
| PVI: | N—Cyclohexylthiophthalimide |
| Ultrasil VN3: | Precipitated silica (Degussa) |
| Gran.: | Granulate |
| V143: | Bis-(2-Ethylamino-4-diethylamino-s-triazine-6-yl)-disulfide |

EXAMPLE 2

Reversion Stability With V 480 As Cross-Linker (Carbon Black As Filler)

|  | 1 | 2 | 3 |
|---|---|---|---|
| RSS 1, Ml 4 = 67 | 100 | 100 | 100 |
| CORAX N 220 | 50 | 50 | 50 |
| ZnO RS | 5 | 50 | 5 |
| Stearic acid | 2 | 2 | 2 |
| Naftolen ZD | 3 | 3 | 3 |
| Vulkanox 4010 NA | 2.5 | 2.5 | 2.5 |
| Vulkanox HS | 1.5 | 1.5 | 1.5 |
| Protektor G 35 | 1 | 1 | 1 |
| Vulkacit MOZ | 1.43 | — | — |
| V 143 | — | 1.29 | — |
| PVI | — | 0.4 | — |
| V 480 | — | — | 4 |
| Sulfur | 1.5 | 1.5 | — |
| $\frac{D_{max} - D_{(max+60')}}{D_{max} - D_{min}}$ (%) |  |  |  |
| 170° C. | 30.0 | 8.5 | 2.3 |

The example shows that reversion stability was obtained using V 480 without sulfur. As reference systems there were used in mixture 1 MOZ in a so-called semi-efficient dosing, which according to the state of the art has been evaluated as very good and in sample 2 there was used the already reversion stable accelerator V 143.

EXAMPLE 3

Temperature Dependence Of The Reversion Behavior Using V 480 (Carbon Black/Silica As Fillers)

|  | 4 | 5 | 6 |
|---|---|---|---|
| RSS 1, ML 4 = 67 | 100 | 100 | 100 |
| CORAX N 220 | 25 | 25 | 25 |
| Ultrasil VN 3 B Gran. | 25 | 25 | 25 |
| ZnO RS | 5 | 5 | 5 |
| Stearic acid | 2 | 2 | 2 |
| Naftolen ZD | 3 | 3 | 3 |
| Vulkanox 4010 NA | 2.5 | 2.5 | 2.5 |
| Vulkanox HS | 1.5 | 1.5 | 1.5 |
| Protektor G 35 | 1.5 | 1.5 | 1.5 |
| V 480 | — | — | 3 |
| Vulkacit MOZ | 1.43 | — | — |
| V 143 | - | 1.29 | — |
| Sulfur | 1.5 | 1.5 | — |
| $\frac{D_{max} - D_{(max+60')}}{D_{max} - 0\,D_{min}}$ (%) |  |  |  |
| 145° C. | 22.4 | 11.3 | 0 |
| 160° C. | 38.8 | 20.9 | 0 |
| 170° C. | 47.4 | 30.3 | 1.9 |
| 180° C. | 52.6 | 38.7 | 4.6 |

Mixtures in which carbon black is partially replaced by silica are especially susceptible to reversion. Mixture 6 shows that V 480 used as a cross-linker, i.e., without sulfur, imparted to the vulcanizate even at the highest vulcanization temperatures the utmost resistance to reversion.

EXAMPLE 4

Vulcanization Stability With Overheating At 170° C. Using V 480

|  | 7 | 8 | 9 |
|---|---|---|---|
| RSS 1, ML 4 = 67 | 100 | 100 | 100 |
| CORAX N 220 | 25 | 25 | 25 |
| Ultrasil Un 3 Gran. | 25 | 25 | 25 |
| ZnO RS | 5 | 50 | 5 |
| Stearic acid | 2 | 2 | 2 |
| Naftolen ZD | 3 | 3 | 3 |
| Vulkanox 4010 NA | 2.5 | 2.5 | 2.5 |
| Vulkanox HS | 1.5 | 1.5 | 1.5 |
| Protektor G 35 | 1 | 1 | 1 |
| Vulkacit MOZ | 1.43 | — | — |
| V 143 | — | 1.29 | — |
| V 480 | — | — | 3 |
| Sulfur | 1.5 | 1.5 | — |
| $\frac{D_{max} - D_{(max+60')}}{D_{max} - D_{min}}$ (%) |  |  |  |
| 170° C. | 44.7 | 28.7 | 2.6 |
| Vulcanization time at 170° C. | *t$_{95\%}$ | t$_{95\%+50'}$ |  |
| Tensile Strength | 17.2 | 16.0 | 19.3 |
|  | 12.5 | 11.2 | 19.7 |
| Modulus 300% | 5.1 | 3.7 | 5.5 |
|  | 3.3 | 2.8 | 5.3 |
| Tear Propagation Resistance | 32 | 16 | 29 |
|  | 6 | 5 | 28 |
| Firestone-Ball Rebound | 54.9 | 52.8 | 53.5 |
|  | 51.3 | 51.7 | 53.2 |

*t$_{95\%}$ means that 95% of the vulcanization agent had been reached; t$_{95\%+50'}$ means that it was heated for a further 50 minutes.

This example shows that with increasing reversion with overheating, namely 50'/170° C. a greater decrease occurs in the physical vulcanization data. This can be seen especially clearly with mixture 7 in the tensile strength and 300% Modulus as well as in the resistance to tear propagation while in contrast mixture 9 in overheating the physical data remained practically unchanged.

Here also V 480 was compared to a semi-EV-system, which according to the state of the art already had been distinguished as resistant to reversion.

EXAMPLE 5

Reversion Stability Using V 480 As Accelerator At a Vulcanization Temperature of 170° C.

|  | 10 | 11 |
|---|---|---|
| RSS 1, ML 4 = 67 | 100 | 100 |
| CORAX N 220 | 50 | 50 |
| ZnO RS | 5 | 5 |
| Stearic acid | 2 | 2 |
| Naftolen ZD | 3 | 3 |
| Vulkanox 4010 NA | 2.5 | 2.5 |
| Vulkanox HS | 1.5 | 1.5 |
| Protektor G 35 | 1 | 1 |
| Vulkacit MOZ | — | 1.43 |
| V 480 | 1.5 |  |
| Sulfur | 0.8 | 1.5 |
| $\frac{D_{max} - D_{(max+60')}}{D_{max} - D_{min}}$ (%) | 0.8 | 29.2 |
| Tensile Strength | 22.6 | 24.3 |
| Modulus 300% | 11.0 | 10.4 |
| Elongation at Break | 480 | 530 |
| Firestone-Ball Rebound | 46.5 | 45.9 |

-continued

|  | 10 | 11 |
|---|---|---|
| Shore A Hardness | 62 | 62 |

Example 5 shows that the combination of 1.5 parts V 480 with 0.8 parts sulfur always remain completely resistant to conversion at 170° C. compared to the corresponding sulfenamide and that with this combination at $t_{95\%}$ practically the same data level is established.

EXAMPLE 6

Influence Of The Sulfur Dosing On The V 480 Accelerator (Vulcanization Temperature: 170° C.)

|  | 12 | 13 | 14 | 15 | 16 | 17 |
|---|---|---|---|---|---|---|
| RSS 1, Ml 4 = 67 | 100 | 100 | 100 | 100 | 100 | 100 |
| CORAX N 220 | 50 | 50 | 50 | 50 | 50 | 50 |
| ZnO RS | 5 | 5 | 5 | 5 | 5 | 5 |
| Stearic acid | 2 | 2 | 2 | 2 | 2 | 2 |
| Naftolen ZD | 3 | 3 | 3 | 3 | 3 | 3 |
| Vulkanox 4010 NA | 2.5 | 2.5 | 2.5 | 2.5 | 2.5 | 2.5 |
| Vulkanox HS | 1.5 | 1.5 | 1.5 | 1.5 | 1.5 | 1.5 |
| Protektor G 35 | 1 | 1 | 1 | 1 | 1 | 1 |
| Vulkacit MOZ | 1.43 | — | — | — | — | — |
| V 143 | — | 1.29 | — | — | — | — |
| PVI | — | 0.4 | — | — | — | — |
| V 480 | — | — | 1.5 | 1.5 | 1.5 | 1.5 |
| Sulfur | 1.5 | 1.5 | 0.8 | 1 | 1.2 | 1.4 |
| $\frac{D_{max} - D_{(max+60')}}{D_{max} - D_{min}}$ (%) | 26.8 | 6.9 | 2.4 | 3.4 | 4.1 | 4.6 |
| $t_{10\%}$ | 3.8 | 4.2 | 3.1 | 2.9 | 2.9 | 2.8 |
| $t_{80}-t_{20\%}$ | 1.4 | 1.4 | 1.6 | 1.6 | 1.5 | 1.5 |
| Vulcanizate data at $t_{95\%}$ Modulus 300% | 11.5 | 12.1 | 11.4 | 12.1 | 12.5 | 13.1 |
| Shore Hardness | 63 | 66 | 63 | 63 | 64 | 65 |

Example 6 shows that an increase of sulfur content beyond 0.8 is possible and leads to increase in modulus without reversion increasing very greatly. Indeed the raising of the sulfur content results in a slight shortening of the scorch properties. This can be counterbalanced through the use of Vulkalent E (see Example 7).

EXAMPLE 7

Effect Of Customary Retarders On The Pre-Vulcanization Time And Reversion Employing V 480

|  | 18 | 19 | 20 | 21 |
|---|---|---|---|---|
| RSS 1, ML (1 + 4) = 67 | 100 | 100 | 100 | 100 |
| CORAX N 220 | 50 | 50 | 50 | 50 |
| ZnO RS | 5 | 5 | 5 | 5 |
| Stearic acid | 2 | 2 | 2 | 2 |
| Naftolen ZD | 3 | 3 | 3 | 3 |
| Vulkanox 4010 NA | 2.5 | 2.5 | 2.5 | 2.5 |
| Vulkanox HS | 1.5 | 1.5 | 1.5 | 1.5 |
| Protektor G 35 | 1 | 1 | 1 | 1 |
| Vulkacit MOZ | 1.43 | — | — | — |
| V 480 | — | 1.5 | 1.5 | 1.5 |
| Sulfur | 1.5 | 0.8 | 0.8 | 0.8 |
| PVI | — | — | 1.2 | — |
| Vulkalent E | — | — | — | 1.2 |
| Scorch time 130° C. min (increase 2 scale divisions | 21.5 | 8.0 | 17.5 | 21.0 |
| Scorch at 170° C. ($t_{10\%}$) | 3.8 | 2.8 | 3.8 | 4.1 |
| Modulus 300% | 10.6 | 11.0 | 8.8 | 13.7 |

EXAMPLE 8

Prolongation Of Scorch And Increase In Modulus Of V 480/Vucalent E—Combination

|  | 22 | 23 | 24 | 25 | 26 |
|---|---|---|---|---|---|
| RSS 1, Ml 4 = 67 | 100 | 100 | 100 | 100 | 100 |
| CORAX N 220 | 50 | 50 | 50 | 50 | 50 |
| ZnO RS | 5 | 5 | 5 | 5 | 5 |
| Stearic acid | 2 | 2 | 2 | 2 | 2 |
| Naftolen ZD | 3 | 3 | 3 | 3 | 3 |
| Vulkanox 4010 NA | 2.5 | 2.5 | 2.5 | 2.5 | 2.5 |
| Vulkanox HS | 1.5 | 1.5 | 1.5 | 1.5 | 1.5 |
| Protektor G 35 | 1 | 1 | 1 | 1 | 1 |
| Vulkacit MOZ | 1.43 | — | — | — | — |
| V 480 | — | 1.5 | 1.5 | 1.5 | 1.5 |
| Vulkalent E | — | — | 0.4 | 0.8 | 1.2 |
| Sulfur | 1.5 | 0.8 | 0.8 | 0.8 | 0.8 |
| Scorch time 130° C., Min. (increase 2 scale divisions) | 21.5 | 8.0 | 12.5 | 16.7 | 21.0 |
| Scorch time 170° C. ($t_{10\%}$), min. | 3.8 | 2.8 | 3.1 | 3.7 | 4.1 |
| Modulus 300% | 10.6 | 11.0 | 11.8 | 12.7 | 13.7 |

EXAMPLE 9

Prolongation Of The Prevulcanization Time By Vulkalent E With The V 480 Vulcanization

|  | 27 | 28 | 29 | 30 |
|---|---|---|---|---|
| RSS 1, ML (1 + 4) = 67 | 100 | 100 | 100 | 100 |
| CORAX N 220 | 25 | 25 | 25 | 25 |
| Ultrasil VN3 Gran. | 25 | 25 | 25 | 25 |
| ZnO RS | 5 | 5 | 5 | 5 |
| Stearic acid | 2 | 2 | 2 | 2 |
| Naftolen ZD | 3 | 3 | 3 | 3 |
| Vulkanox 4010 NA | 2.5 | 2.5 | 2.5 | 2.5 |
| Vulkanox HS | 1.5 | 1.5 | 1.5 | 1.5 |
| Protektor G 35 | 1 | 1 | 1 | 1 |
| Vulkacit MOZ | 1.43 | — | — | — |
| PVI | — | — | 1.2 | — |
| V 480 | — | 3 | 3 | 1.5 |
| Vulkalent E | — | — | — | 1.2 |
| Sulfur | 1.5 | 0.8 | 0.8 | 0.8 |
| Scorch time 130° C., Min (increase 2 scale divisions) | 29.5 | 16.1 | 28.5 | 30.0 |
| Scorch time 170° C. | 4.5 | 3.6 | 4.2 | 4.7 |
| Modulus 300% | 5.3 | 6.4 | 6.4 | 8.6 |

Example 9 shows the effectiveness of the retarder Vulkalent E in the case of a blend of carbon black and silica. Using 1.5 parts V 480, 0.8 parts sulfur and 1.2 parts of Vulkalent E there were obtained MOZ prevulcanization times without further doing anything. The reversion properties of V 480 vulcanization also were not negatively influences by the inclusion of retarders, no more than were the physical data of the vulcanizate.

EXAMPLE 10

V 480 As Accelerator In SBR

|  | 31 | 32 | 33 |
|---|---|---|---|
| SBR 1712 | 137.5 | 137.5 | 137.5 |
| CORAX N 339 | 60 | 60 | 60 |
| ZnO RS | 3 | 3 | 3 |
| Stearic acid | 2 | 2 | 2 |
| Protektor G 35 | 1 | 1 | 1 |
| Vulkanox 4010 NA | 1.5 | 1.5 | 1.5 |
| Vulkacit D | 0.5 | 0.5 | — |
| Vulkacit CZ | 1.45 | — | — |
| V 480 | — | 1.5 | 1.5 |

-continued

|  | 31 | 32 | 33 |
|---|---|---|---|
| Sulfur | 1.6 | 1.5 | 1.5 |
| $\frac{D_{max} - D_{(max+60')}}{D_{max} - D_{min}}$ (%) | 10.5 | 7.3 | 8.3 |
| at 165° C. | | | |
| Tensile Strength | 20 | 19.2 | 23.1 |
| Modulus 300% | 10.1 | 11.4 | 10.9 |
| Elongation at Break | 480 | 430 | 460 |
| Shore A Hardness | 63 | 65 | 64 |

Example 10 shows that V 480 also exerts a positive influence on the resistance to reversion in otherwise already reversion resistant SBR mixtures.

EXAMPLE 11

Resistance To Reversion Of SBR-Vulcanization With V 480

|  | 33 | 34 |
|---|---|---|
| SBR 1500 | 100 | 100 |
| CORAX N 220 | 50 | 50 |
| ZnO RS | 5 | 5 |
| Stearic acid | 2 | 2 |
| Naftolen ZD | 3 | 3 |
| Vulkanox 4010 NA | 2.5 | 2.5 |
| Vulkanox HS | 1.5 | 1.5 |
| Protektor G 35 | 1 | 1 |
| Vulkacit CZ | 1.5 | — |
| V 480 | — | 1 |
| Sulfur | 1.8 | 1.8 |
| $\frac{D_{max} - D_{(max+60')}}{D_{max} - D_{min} (170° C.)}$ (%) | 12.1 | 9.1 |
| Vulcanizate data at $t_{95\%}$: | | |
| Tensile Strength | 20.2 | 21.8 |
| Modulus 300% | 10.6 | 11.1 |
| Elongation at Break | 450 | 460 |
| Resistance To Tear Propagation | 13 | 14 |
| Shore A Hardness | 63 | 64 |

This sample shows that V 480 still further improves the reversion properties of the otherwise already slightly reversion susceptible SBR 1500.

EXAMPLE 12

V 480 In Perbuban (Nitrile Rubber)

|  | | |
|---|---|---|
| Perbunan N 3307 NS | 100 | 100 |
| CORAX N 220 | 50 | 50 |
| ZnO RS | 5 | 5 |
| Stearic acid | 1 | 1 |
| Ingralen 450 | 5 | 5 |
| Mesamoll | 10 | 10 |
| Vulkacit CZ | 1.3 | — |
| V 480 | — | 1.5 |
| Sulfur | 1.8 | 1.8 |
| $\frac{D_{max} - D_{(max+60')}}{D_{max} - D_{min\ at\ 170°\ C.}}$ (%) | 9.5 | 6.9 |
| Vulcanizate data: | | |
| Tensile Strength | 19.5 | 18.8 |
| Modulus 300% | 9.2 | 11.3 |
| Elongation at Break | 480 | 380 |
| Shore A Hardness | 64 | 65 |

As the example shows the inclusion of V 480 in place of a sulfenamide imparts further advantages in regard to resistance to reversion.

EXAMPLE 13

V 480 In EPDM

|  | | |
|---|---|---|
| Buna AP 541 | 100 | 100 |
| CORAX N 220 | 50 | 50 |
| ZnO RS | 5 | 5 |
| Stearic acid | 1 | 1 |
| Ingraplast NS | 10 | 10 |
| Vulkacit Thiuram | 1 | — |
| Vulkacit Mercapto | 0.5 | — |
| V 480 | — | 2.5 |
| Sulfur | | 1 |
| $\frac{D_{max} - D_{(max+60')}}{D_{max} - D_{min\ at\ 170°\ C.}}$ (%) | 3.3 | 0 |
| Vulcanizate Data: | | |
| Tensile Strength | 16.0 | 16.0 |
| Modulus 300% | 14.4 | 14.0 |
| Elongation at Break | 320 | 350 |
| Shore A Hardness | 72 | 69 |

For EPDM also through the inclusion of V 480 there results at the same regulation of the vulcanizate data the possibility still for further increase of the resistance to reversion.

EXAMPLE 14

Simultaneous Use Of V 480 And Si 69

|  | | |
|---|---|---|
| RSS 1, ML 4 = 67 | 100 | 100 |
| CORAX N 220 | 50 | 50 |
| ZnO RS | 5 | 5 |
| Stearic acid | 2 | 2 |
| Naftolen ZD | 3 | 3 |
| Vulkanox 4010 NA | 2.5 | 2.5 |
| Vulkanox HS | 1.5 | 1.5 |
| Protektor G 35 | 1 | 1 |
| Vulkacit MOZ | 1.43 | — |
| V 480 | — | 1.5 |
| Si 69 | — | 1.5 |
| Sulfur | 1.5 | 0.4 |
| $\frac{D_{max} - D_{(max+60')}}{D_{max} - D_{min\ at\ 170°\ C.}}$ (%) | 29.7 | 0 |
| Vulcanizate data: | | |
| Tensile Strength | 25.1 | 22.0 |
| Modulus 300% | 10.2 | 10.8 |
| Firestone-Ball Rebound | 45.2 | 44.2 |
| Shore A Hardness | 63 | 62 |
| Goodrich-Flexometer delta T Center °C. | 159 | 136 |

If there is replaced a portion of the sulfur (0.8 parts) by sulfur donors as for example polysulfidic silane, there likewise result an extraordinarily reversion resistance by the example above. Furthermore, there occurs an extraordinary lowering of the build up of heat.

EXAMPLE 15

V 480 Cross-Linking Of Epoxidized Natural Rubber Using Carbon Black And Silica As Filler

|  | 1 | 2 |
|---|---|---|
| ENR 50 | 100 | 100 |
| CORAX N 330 | 25 | 25 |
| Ultrasil VN 3 Gran. | 25 | 25 |

-continued

|  | 1 | 2 |
|---|---|---|
| ZnO RS | 5 | 5 |
| Stearic acid | 2 | 2 |
| Vulkanox HS | 2 | 2 |
| V 480 | — | 3 |
| Vulkacit MOZ | 2.4 | — |
| Vulkacit Thiuram | 1.6 | — |
| Sulfur | 0.3 | 0.3 |
| Tensile strength | 15.1 | 15.6 |
| Modulus 100% (MPa) | 8.4 | 11.0 |
| Further Tear Propagation DIN 53 507 (N/mm) | 8 | 8 |
| Shore A Hardness DIN 53 505 23° C. | 82 | 89 |

EXAMPLE 16

V 480 Cross-Linking Of Epoxidized Natural Rubber Using Carbon Black Files

|  | 1 | 2 |
|---|---|---|
| ENR | 100 | 100 |
| CORAX N 220 | 50 | 50 |
| ZnO RS | 5 | 5 |
| Stearic acid | 2 | 2 |
| Vulkanox HS | 2 | 2 |
| V 480 | — | 4 |
| Vulkacit MOZ | 2.4 | — |
| Vulkacit Thiuram | 1.6 | — |
| Sulfur | 0.3 | 0.3 |
| Tensile Strength DIN 53 504 Ring 1 (MPa) | 18.7 | 27.0 |
| Modulus 300% (MPa) | 18.0 | 19.0 |
| Resistance to further propagation DIN 53 507 (N/mm) | 12 | 12 |
| Shore A Hardness DIN 53 505 23° C. | 75 | 80 |

What is claimed is:

1. A vulcanizable composition comprising bis-(2-ethylamino-4-diethylamino-s-triazin-6-yl)-tetrasulfide as an accelerator and a vulcanizable rubber selected from the group consisting of natural rubber, isoprene rubber, styrene-butadiene rubber, isobutylene-isoprene rubber, ethylene-propylene terpolymer rubber, nitrile rubber, halogen containing rubber, and natural rubber which is epoxidized up to 75%, the amount of triazinyl tetrasulfide being 0.3 to 15 parts based on 100 parts of the rubber.

2. A sulfur($S_8$)-free vulcanizable composition comprising bis-(2-ethylamino-4-diethylamino-s-triazin-6-yl)-tetrasulfide as a cross-linker and a vulcanizable rubber selected from the group consisting of natural rubber, isoprene rubber, styrene-butadiene rubber, isobutylene-isoprene rubber, ethylenepropylene terpolymer rubber, nitrile rubber, halogen containing rubber, and natural rubber which is epoxidized up to 75%, the amount of triazinyl tetrasulfide being 0.3 to 10 parts based on 100 parts of rubber.

3. A vulcanizable composition comprising bis-(2-ethylamino-4-diethylamino-s-triazin-6-yl)-tetrasulfide as an accelerator, at least one member of the group consisting of an additional accelerator, a retarder and an organosilane and a vulcanizable rubber selected from the group consisting of natural rubber, isoprene rubber, styrene-butadiene rubber, isobutyleneisoprene rubber, ethylene-propylene terpolymer rubber, nitrile rubber, halogen containing rubber, and a natural rubber which is epoxidized up to 75%, the amount of triazinyl tetrasulfide being 0.3 to 15 parts based on 100 parts of rubber.

4. The product obtained by vulcanizing the composition of claim 1.

5. The composition according to claim 1 wherein the rubber is natural rubber.

6. The product obtained by vulcanizing the composition of claim 2.

7. A vulcanizable composition according to claim 1 containing (N-trichloromethylthiophenylsulfonyl)-benzene, the molar ratio of the triazinyl tetrasulfide to the phenylsulfonylbenzene being 1:1 and the amount of sulfur being 0.2 to 4 part based on 100 parts of the rubber.

8. A vulcanizable composition according to claim 7 containing 0.6 to 1.8 parts of sulfur per 100 parts of rubber.

9. A vulcanizable composition according to claim 2 wherein the rubber is natural rubber.

10. A vulcanizable composition according to claim 1 wherein the rubber is styrene-butadiene rubber.

11. A vulcanizable composition according to claim 1 wherein the rubber is nitrile rubber.

12. A vulcanizable composition according to claim 1 wherein the rubber is ethylene-propylene terpolymer rubber.

* * * * *